United States Patent
Lo

(10) Patent No.: US 11,654,168 B2
(45) Date of Patent: May 23, 2023

(54) GANODERMA LUCIDUM FERMENTED BEVERAGE PRODUCT AND METHOD FOR MAKING THE SAME

(71) Applicant: Ling Lan Lo, Sheung Wan (HK)

(72) Inventor: Ling Lan Lo, Sheung Wan (HK)

( * ) Notice: Subject to any disclaimer, the term of this patent is extended or adjusted under 35 U.S.C. 154(b) by 102 days.

(21) Appl. No.: 17/228,711

(22) Filed: Apr. 13, 2021

(65) Prior Publication Data

US 2022/0323522 A1  Oct. 13, 2022

(51) Int. Cl.
| | |
|---|---|
| A61K 36/074 | (2006.01) |
| A61K 47/26 | (2006.01) |
| A61K 47/46 | (2006.01) |
| A61K 31/4745 | (2006.01) |
| A23L 2/38 | (2021.01) |
| A23L 33/10 | (2016.01) |
| A23L 31/00 | (2016.01) |
| A23L 2/60 | (2006.01) |

(52) U.S. Cl.
CPC ............ *A61K 36/074* (2013.01); *A23L 2/382* (2013.01); *A23L 2/60* (2013.01); *A23L 31/00* (2016.08); *A23L 33/10* (2016.08); *A61K 31/4745* (2013.01); *A61K 47/26* (2013.01); *A61K 47/46* (2013.01); *A23V 2002/00* (2013.01); *A61K 2236/19* (2013.01); *A61K 2236/31* (2013.01); *A61K 2236/331* (2013.01)

(58) Field of Classification Search
CPC ...... A61K 36/074; A61K 47/26; A61K 47/46; A61K 31/4745; A61K 2236/19; A61K 2236/31; A61K 2236/331; A23L 2/38; A23L 2/60; A23L 33/10; A23L 31/00; A23L 2/382; A23V 2002/00
See application file for complete search history.

(56) References Cited

U.S. PATENT DOCUMENTS

| | | |
|---|---|---|
| 6,316,002 B1 | 11/2001 | Liu |
| 6,468,542 B2 | 10/2002 | Liu |
| 2016/0022749 A1 | 1/2016 | Chen |
| 2018/0125879 A1 | 5/2018 | Sugita |

OTHER PUBLICATIONS

Aleksandra Sknepnek, Milena Pantić, Danka Matijašević, Dunja Miletić, Steva Lević, Viktor Nedović, Miomir Nikšic. Novel Kombucha Beverage from Lingzhi or Reishi Medicinal Mushroom Ganoderma lucidum with Antibacterial and Antioxidant Effects. International J. of Medicinal Mushrooms, 20(3):243-258, 2018 (Year: 2018).*

* cited by examiner

*Primary Examiner* — Manjunath N Rao
*Assistant Examiner* — Victoria Ronice Brooks

(57) ABSTRACT

A method for manufacturing a *Ganoderma Lucidum* fermented beverage product (GLfb) is provided. It has found that *Ganoderma lucidum* contains high quantity of natural Pyrroloquinoline Quinone (PQQ). Free radicals generated by ischemic or hypoxic conditions have been found to be a significant cause of myocardial damage leading to myocardial death. PQQ has been reported to act as a free radical scavenger. In particular, PQQ has been reported to be effective in neutralizing superoxide and hydroxyl radicals.

1 Claim, No Drawings

GANODERMA LUCIDUM FERMENTED BEVERAGE PRODUCT AND METHOD FOR MAKING THE SAME

FIELD OF THE INVENTION

It is well known that Pyrroloquinoline Quinone (PQQ) is the most powerful immunotherapeutic substance that human beings have found on the earth in this century. The most powerful natural element of immune enhancement to mammal. It has found that *Ganoderma lucidum* contains high quantity of natural PQQ. The present invention provides a method for enhancing a mammal immune system, particularly athlete immune system by oral administration of *Ganoderma lucidum* fermented beverage product (GLfb) having PQQ.

BACKGROUND OF THE INVENTION

Physical exercise is characterized by an increase in oxygen consumption of the whole body. During oxygen metabolism, much of the oxygen consumed is bound to hydrogen during oxidative phosphorylation forming water. However, 4% to 5% of the oxygen consumed during respiration is not completely reduced to water, instead forming free radicals. Thus, the increase of oxygen consumption during an athletic competition generates a concomitant increase of free radical production and creates molecular cell damage such as peroxidation of lipids.

During an intense physical activity or overload training, the antioxidant capacity of the organism is not sufficient to limit free radical production, resulting in an increase of oxidative stress that can be detrimental to the body. The detrimental effect in the body caused by the oxidative stress may involve unbalanced non-enzymatic or enzymatic antioxidant status, and cellular and muscular damages.

Muscle and joint inflammation often result from intense exercise, thus triggering tissue infiltration of neutrophils and subsequent release of reactive oxygen species during the "oxidative burst" characteristic of activated neutrophils mediated by the immune response. Enhanced antioxidant intake in humans has been reported to decrease the risk of developing specific forms of cancer and to enhance immune function.

Free radicals generated by ischemic or hypoxic conditions have been found to be a significant cause of myocardial damage leading to myocardial death. As such, administration of Pyrroloquinoline Quinone (PQQ), administered in vivo is an effective treatment for inhibiting or preventing myocardial oxidative stress free radical damage, either by PQQ-mediated free radical scavenging, or by inhibition of free radical generation. PQQ has been reported to act as a free radical scavenger, capable of carrying out thousands of electron transfers without undergoing molecular breakdown. In particular, PQQ has been reported to be effective in neutralizing superoxide and hydroxyl radicals. PQQ, a cofactor of dehydrogenase and amine oxidase, increases the production of the nerve growth factor (NGF), and protects N-methyl-D-aspartate (NMDA) receptors by a direct oxidation of the receptor redox site. PQQ also protects neurons from NMDA toxicity by suppressing peroxynitrite and stimulates NGF production. Furthermore, PQQ acts as an antioxidant against lipid peroxidation. Thus, it is likely that PQQ improves cognitive deficit caused by oxidative stress, similarly to vitamin E.

The main biological functions of PQQ included: (1) stimulating the growth of microorganisms, plants, animals and human cells; (2) acting as an essential nutrient for animal growth, development and reproduction; (3) removing excessive free radicals and protecting the body from oxidative damage; (4) providing neurotrophic and protective effects.

SUMMARY OF THE INVENTION

The present invention provides a method for manufacturing a *Ganoderma lucidum* fermented beverage product (GLfb). This method requires combining *Ganoderma lucidum* having Pyrroloquinoline Quinone therein with about 4%, by weight, of crystal sugar, about 6%, by weight, of honey, and about 6% by weight, of water to form a mixture. It is boiled for one hour to form a mash and liquid is then extracted.

The liquid is braised in an airtight container for about 15 days to form a braised liquid. It requires fermentation with about 400%, by weight, of water in a fermentation tank for about 120 days to form a first fermented liquid. It is then fermented with about 25%, by weight, of *Ganoderma lucidum* having Pyrroloquinoline Quinone therein in the said fermentation tank for about 90 days to form a second time fermented liquid. It is further fermented with about 6%, by weight, of honey, about 4%, by weight, of crystal sugar, and about 1000%, by weight, of water at room temperature for about 30 days to form a third time fermented liquid.

Stirring of the said third time fermented liquid is required for about 10 days and fermenting the said third time fermented liquid for about 365 days to form a fourth time fermented liquid. It is, finally, blend diluted to form the *Ganoderma lucidum* fermented beverage product (GLfb).

DETAILED DESCRIPTION OF THE INVENTION

Below are general description of the inventive steps which lead to the product of the *Ganoderma lucidum* fermented beverage product (GLfb).

I. Boiling of *Ganoderma lucidum* with ingredients: *Ganoderma lucidum* having Pyrroloquinoline Quinone therein was combined with about 4%, by weight, of crystal sugar, about 6%, by weight, of honey, and about 6% by weight, of water to form a mixture. It was boiled for one hour to form a mash. Liquid was then extracted from the mash.

II. First time fermentation: The liquid was braised in an airtight container for about 15 days to form a braised liquid which was fermented with about 400%, by weight, of water in a fermentation tank for about 120 days to form a first fermented liquid.

III. Second time fermentation: The first time fermented liquid was then fermented with about 25%, by weight, of *Ganoderma lucidum* having Pyrroloquinoline Quinone therein in the said fermentation tank for about 90 days to form a second time fermented liquid.

IV. Third time fermentation: The second time fermented liquid was further fermented with about 6%, by weight, of honey, about 4%, by weight, of crystal sugar, and about 1000%, by weight, of water at room temperature for about 30 days to form a third time fermented liquid.

V. Third time fermentation: The third time fermented liquid was stirred for about 10 days It was then fermented for about 365 days to form a fourth time fermented liquid.

VI. Blend dilution: Finally, the fourth time fermented liquid was blend diluted to form the *Ganoderma lucidum* fermented beverage product (GLfb).

Manufacturing Examples

1. Eighty (80) kg of *Ganoderma lucidum* having Pyrroloquinoline Quinone therein was combined with three (3) kg of crystal sugar, five (5) kg of honey, and five (5) kg of water to form a mixture. It was boiled for one hour to form a mash. Liquid was then extracted from the mash.

2. The liquid was braised in an airtight container for about 15 days to form a braised liquid which was fermented with three hundred eighty (380) kg of water in a fermentation tank for about 120 days to form a first fermented liquid.

3. The first time fermented liquid was then fermented with twenty (20) kg of *Ganoderma lucidum* having Pyrroloquinoline Quinone therein in the said fermentation tank for about 90 days to form a second time fermented liquid.

4. The second time fermented liquid was further fermented with five (5) kg of of honey, three (3) kg of crystal sugar, and eight hundred (800) kg of water at room temperature for about 30 days to form a third time fermented liquid.

5. The third time fermented liquid was stirred for about 10 days It was then fermented for about 365 days to form a fourth time fermented liquid.

6 The fourth time fermented liquid was blend diluted to form the *Ganoderma lucidum* fermented beverage product (GLfb).

Experimental Examples

In this study, the *Ganoderma lucidum* fermented beverage product (GLfb) was used in athletes to observe its effect on improving immunity and improving functional levels.

1. Materials and Methods 1.1 Test Subjects

The test subjects are 30 outstanding ski athletes, 14 males and 16 females. Among them, 8 were short-track speed skating, 8 were speed skating, 4 were figure skating, 6 were skiing, and 4 were ice hockey.

1.2 Test Drug

The *Ganoderma lucidum* fermented beverage product (GLfb) and a placebo having the same color, packaging and taste are the test drug in this study. The main ingredients of the *Ganoderma lucidum* fermented beverage product (GLfb) are *Ganoderma lucidum* and honey.

1.3 Experiment Method

A randomized single-blind, placebo-controlled experimental method was adopted. That is, the experimental group takes 50 mL of the *Ganoderma lucidum* fermented beverage product (GLfb) after meals in every morning and evening for a total of 50 days. The control group takes the placebo of the same dose. The physiological and biochemical indicators are tested before, during and after the related training courses. The test results before the experiment showed that there was no significant difference between the experimental group and the control group in sports performance and overall functional level.

1.4 Test Index 1.4.1 Immune Index

The FACSCALIBUR flow cytometer produced by American B-D Company was used to measure NK cells. The reagent used was the product of American B-D Company CD3/CD16-56 double-labeled fluorescent antibody. Immunoglobulin G (IgG), Immunoglobulin M (IgM), Immunoglobulin A (IgA) were determined with ARRAY360 specific protein analyzer from BECKMAN, USA. The reagents used were products of BECKMAN. The white blood cell count was measured by optical microscopy.

1.4.2 Athletic Ability Index

The Analyzer "780" semi-automatic biochemical analyzer produced by CRONY, Italy was used to measure BUN (blood Urea), CK (serum creatine kinase), GOT Glutamic oxaloacetic transaminase), GPT (glutamic pyruvic transaminase), CRE (creatinine), Hb (Hemoglobin) and other indicators. The reagents used are the products of Beijing Zhongsheng Biological Engineering High-tech Company. Serum testosterone (T) was determined by radioimmunoassay with a CAT-R16 radioimmunoassay counter produced by Xi'an Liya Company. The reagent was the product of the Shanghai branch of the American Depp company: Testosterone determination box.

1.5 Statistical Methods

The collected data are all processed on a IBM586 computer using SPSS statistical software, and the relevant data is compared with t-test.

2. Result 2.1 The influence of GLfb on the immunity of ski athletes.

2.1.1 GLfb can effectively regulate and improve the body's immunity. In this study, the immunoglobulin molecules IgG, IgM, and IgA in the experimental group were significantly improved compared with the control group after treatment ($P<0.01$). The control group showed a slight downward trend. See Table 1.

TABLE 1

Comparison of IgG, IgM, IgA between the experimental group and the control group before and after the experiment

| Group | Sample quantity | Test time | IgG (g/L) | IgM (g/L) | IgA (g/L) |
| --- | --- | --- | --- | --- | --- |
| Control Group | 15 | before experiment | 11.57 ± 2.46 | 1.20 ± 0.37 | 1.73 ± 0.51 |
| | | after experiment | 10.71 ± 1.98 | 1.05 ± 0.35 | 1.72 ± 0.44 |
| | | difference | −1.12 ± 0.93 | −0.15 ± 0.12 | −0.14 ± 0.18 |
| Experimental Group | 14 | before experiment | 11.90 ± 1.37 | 1.32 ± 0.45 | 2.01 ± 0.81 |
| | | after experiment | 12.02 ± 1.05 | 1.41 ± 0.59 | 2.04 ± 0.89 |
| | | difference | 0.28 ± 1.39** | 0.12 ± 0.26** | 0.16 ± 0.54* |

*$P < 0.05$,

**$P < 0.01$ compared with the control group 2.1.2 The GLfb can increase the number of immune cells. In this study, the number of natural killer cells (NK cells) and white blood cells (WBC) in the experimental group increased significantly after treatment (P<0.01). The change in the control group was not obvious. See Table 2.

TABLE 2

Comparison of NK cells and WBC between the experimental group and the control group before and after the experiment

| Group | Sample quantity | Test time | NK cells | WBC × 10/L |
|---|---|---|---|---|
| Control Group | 13 | before experiment | 26.51 ± 7.61 | 4.68 ± 1.03 |
| | | after experiment | 25.46 ± 6.43 | 4.60 ± 1.05 |
| | | difference | −0.52 ± 3.31 | −0.10 ± 1.51 |
| Experimental Group | 14 | before experiment | 21.63 ± 6.43 | 4.19 ± 0.75 |
| | | after experiment | 27.46 ± 8.63 | 6.27 ± 2.51**·· |
| | | difference | 4.18 ± 2.29** | 2.22 ± 2.81** |

**P < 0.01 compared with the control group
**··P < 0.01 compared with oneself 2.2 The influence of the GLfb on the overall performance of ski athletes.

2.2.1 The results of this experimental study show that the GLfb can not only improve the overall performance level of ski athletes, but also accelerate the recovery of fatigue after exercise. In the function test of the same load, the experimental group is taking medicine. The BUN before and after decreased significantly (P<0.05). The control group did not change significantly (P>0.05). Before the test, the experimental group and the control group had significant differences in CK activity (P<0.05). This may be related to the fact that there are fewer experimental objects and greater individual differences. After medication, there was no significant difference in CK activity between the two groups (P>0.05). This shows that the GLfb has a positive effect on reducing CK activity. See Table 3.

TABLE 3

Comparison of BUN and CK between the experimental group and the control group before and after the experiment

| Group | Sample quantity | Test time | BUN (mmol/L) | CK (U/L) |
|---|---|---|---|---|
| Control Group | 13 | before experiment | 8.77 ± 3.57 | 141.00 ± 73.67 |
| | | after experiment | 8.51 ± 2.10 | 135.54 ± 58.38 |
| | | difference | −0.17 ± 3.50 | −5.64 ± 56.15 |
| Experimental Group | 15 | before experiment | 8.22 ± 2.73 | 199.64 ± 76.38*·· |
| | | after experiment | 6.53 ± 2.44*·· | 164.29 ± 93.52·· |
| | | difference | −1.68 ± 2.93 | −35.36 ± 60.50 |

*··P < 0.05:
···P < 0.05 compared with the control group
*P < 0.05:
··P < 0.05 compared with oneself 2.2.2 The serum testosterone index (T) of the experimental group and the control paper increased after medication. But from the perspective of improvement, the experimental group was significantly better than the control group (P<0.01). The serum testosterone (T) of the female athletes in the control group has a slight downward trend. See Table 4, 5.

TABLE 4

Comparison of male serum testosterone (T) between the experimental group
and the control group before and after the experiment. Unit: (ng/dl)

| Group | Sample quantity | before experiment | after experiment | difference |
|---|---|---|---|---|
| Control Group | 6 | 788.56 ± 360.21 | 976.74 ± 208.56 | 188.18 ± 256.00 |
| Experimental Group | 7 | 490.90 ± 250.32 | 911.32 ± 165.92**△ | 420.42 ± 256.22*△ |

*△P < 0.05 compared with the control group
**△P < 0.01 compared with oneself

TABLE 5

Comparison of female serum testosterone (T) between the experimental
group and the control group before and after the experiment. Unit: (ng/dl)

| Group | Sample quantity | before experiment | after experiment | difference |
|---|---|---|---|---|
| Control Group | 5 | 80.30 ± 11.42 | 75.54 ± 9.41 | −5.10 ± 4.49 |
| Experimental Group | 8 | 64.80 ± 20.49 | 95.94 ± 11.26 | 31.14 ± 27.33** |

**P < 0.01 compared with the control group 2.2.3 The hemoglobin (Hb) indicators collected in this study showed that after the treatment of the experimental group, Hb had a tendency to increase, but there was no significant change (P>0.05). See Table 6.

TABLE 6

Comparison of hemoglobin (Hb) between the experimental group and
the control group before and after the experiment. Unit: (g/100 mL)

| Group | Sample quantity | before experiment | after experiment | difference |
|---|---|---|---|---|
| Control Group | 15 | 12.89 ± 1.28 | 12.68 ± 1.20△ | 0.43 ± 1.03 |
| Experimental Group | 15 | 13.32 ± 0.94 | 13.29 ± 0.82△ | 0.70 ± 1.25△△ |

△P > 0.05 compared with the control group
△△P > 0.05 compared with oneself

3. Discussion

In the old days, the internal operating mechanism between the immune system, the nervous system and the internal environment system is not fully understood. However, a large amount of data show that there is mutual regulation between the immune system, the nervous system and internal environment system. Not only can the nervous system regulate the immune process, the products of the immune system can also regulate the function of the nervous-internal environment system. The tension before the game and the metabolic toxic products of heavy exercise make the internal environment imbalance, inhibit the nerve and immune functions and increase the body's susceptibility. Therefore, improving the activity of the immune system and maintaining the stability of the immune-nerve-internal environment circuit can enhance the body's adaptability and improve athletic ability.

Immunoglobulin molecules (immunoglobulin, Ig) are the main members of the immune family, and are the most important immune molecules that exert immune functions in the humoral immune response. According to the difference of its H chain antigen, it can be divided into IgG, IgM, IgA, IgD, IgE. Different Ig differ in their synthesis site, synthesis time, serum content, distribution, half-period and biological activity. IgG must be synthesized and secreted by plasma cells in the spleen and lymph nodes, which account for about 75% of the total serum Ig, and play an important role in natural passive immunity. In addition, IgG also has the functions of opsonizing valley phagocytosis, antibody dependent cell mediated cytotoxicity (ADCC) and binding to SPA. Therefore, IgG plays a major role in the body's immune protection. IgA is mainly produced by mucosal-associated lymphoid tissues, accounting for about 10% of the total serum Ig. Secreted IgA binds to the corresponding pathogenic microorganisms to inhibit its adsorption to susceptible cells. In addition, secreted IgA also has the immune exclusion function that combines a large number of soluble antigens in the diet and the pyrogenic substances released by the normal intestinal flora or pathogenic microorganisms to prevent them from entering the blood. IgM is the Ig with the largest molecular weight in serum, accounting for about 10% of the total serum Ig. Since IgM is produced in the early stage of the immune response, and the hemolysis with the participation of complement is more than 500 times stronger than that of IgG, and after activation of complement, it plays an opsonizing phagocytosis through C3b, C4b and other fragments, so IgM occupies an important position in the body's early immune protection. In this study, the IgG and IgM levels of the experimental group were significantly higher than those of the control group (P<0.01). IgA also increased significantly (P<0.05). This suggests that the GLfb has a positive effect on improving the immunoglobulin (Ig) of ice-time athletes.

Natural killer cells (NK cells) and white blood cells (WBC) are important immune monitoring indicators. When IgG binds to target cells and binds to CD16 of NK cells, it can cause cell-to-target cell killing (ADCC). Therefore, NK cells are important mediators of ADCC. NK cells can also synthesize and secrete IFN-y under certain conditions. IFN-y can kill infected pathogenic microorganisms. Leukocytes (WBC) are produced by bone marrow and lymphoid tissues. Because the neutrophils and monocytes in WBC can process and promote antigens, and lymphocytes are the main body of the body's immune function. Therefore, the number of WBC reflects the body's immune level to a certain extent. The statistical results showed that after the medication, the number of NK cells and WBC in the experimental group increased significantly compared with the control group within the normal threshold. This shows that the GLfb can effectively increase the number of immune cells.

Recently, blood urea (BUN) and serum creatine kinase (CK) have become the main biochemical indicators for monitoring athletes' functional level, exercise load and fatigue. BUN is the final product of the catabolism of proteins and amino acids in the body. Proteins and amino acids remove amino groups during catabolism. Ammonia is converted into non-toxic urea in the liver and then circulated through the blood to the kidneys to be excreted. During prolonged and strenuous exercise, the energy balance in muscles is disrupted, muscle glycogen reserves are reduced, protein and amino acids in the body participate in the process of glycogen energy storage and replenishment, catabolism is accelerated, and pyruvate—the glucose cycle is strengthened, causing BUN to increase.

The increase in blood BUN indicates the extent to which the body uses protein for energy. When protein is used as an energy reserve, the extent to which it is used is one of the signs of the body's adaptability. The stronger the body's adaptability, the less protein it uses, and the less BUN produced in the body. Conversely, when the body's adaptability is weak, more protein will be used and BUN production will increase. Creatine kinase (CK) catalyzes the reaction of ADP+CP→ATP+C to ensure the energy supply during intense muscle contraction and the resynthesis of ATP and CP after exercise.

During exercise, due to hypoxia, accumulation of metabolites and relatively insufficient energy supply, the permeability of the muscle cell membrane is increased or the muscle cell membrane is damaged, which promotes the release of enzymes from the cell, the enzyme enters the blood circulation, and the activity of CK increases. The level of CK activity reflects the degree of muscle work. In this study, the test results under the same load condition showed that the decrease of BUN and CK in the experimental group was significantly greater than that in the control group ($P<0.05$). This hint the *Ganoderma lucidum* fermented beverage product has a positive effect on improving the functional level of ski athletes and promoting the recovery of fatigue.

Serum testosterone (T) has always been an indicator of concern in sports training. Testosterone is one of the main anabolic hormones in the body. It can stimulate tissue uptake of amino acids, promote nucleic acid and protein synthesis, promote muscle fiber and bone growth, stimulate erythropoietin secretion and accelerate fatigue recovery after exercise. In this study, the experimental group had a significant increase in serum testosterone after medication. The change in the control group was not obvious, and the women in the control group showed a slight downward trend. Relevant studies have shown that: the body's exercise capacity is highly positively correlated with serum testosterone. Other studies have shown that the changes in serum testosterone caused by exercise are mainly affected by factors such as exercise density, load intensity, load volume, and duration. Appropriate exercise training can increase or not change serum testosterone in a quiet state. However, long-term high-volume training or over-training, serum testosterone often decreases. The mechanism is mainly due to the fact that the function of the hypothalamus-pituitary-gonadal axis (HPG) is inhibited in multiple links due to training. Therefore, improving the function of the HPG axis can better inhibit the reduction of exercise-induced serum testosterone.

This research group believes that the main mechanism why the GLfb can improve the body's immunity and improve the overall functional level is that the GLfb regulates the function of invigorating the kidney and invigorating the spleen, improves the function of the HPG axis and the level of muscle energy metabolism, so that BUN, CK, T The production trend is positive. Its effective traditional Chinese medicine components can increase the content of immunoglobulin (Ig) and the number of NK cells and WBC, effectively improve the activity of the body's immune system, and better maintain the stability of the immune-nerve-endocrine circuit, so that It fully plays a regulatory role in the body's metabolism, inhibits the generation of free radicals, accelerates the elimination of foreign bodies in the body, enhances the body's adaptability and disease resistance, so as to enhance the body's exercise capacity, and accelerates the recovery of fatigue after exercise.

What is claimed is:

1. A method for manufacturing a *Ganoderma lucidum* fermented beverage product comprising: combining *Ganoderma lucidum* having Pyrroloquinoline Quinone therein with 4% by weight, of crystal sugar, 6% by weight of honey, and 6% by weight of water to form a mixture; boiling said mixture for one hour to form a mash; extracting liquid from said mash; braising said liquid in an airtight container for 15 days to form a braised liquid; fermenting said braised liquid with 400% by weight of water in a fermentation tank for 120 days to form a first fermented liquid; fermenting said first time fermented liquid with 25% by weight of *Ganoderma lucidum* having Pyrroloquinoline Quinone therein in the said fermentation tank for 90 days to form a second time fermented liquid; fermenting the said second time fermented liquid with 6% by weight of honey, 4% by weight of crystal sugar, and 1000% by weight of water at room temperature for 30 days to form a third time fermented liquid; stirring the said third time fermented liquid for 10 days and fermenting the said third time fermented liquid for 365 days to form a fourth time fermented liquid; diluting the said fourth time fermented liquid to form the *Ganoderma lucidum* fermented beverage product.

* * * * *